United States Patent
Simmons et al.

(10) Patent No.: US 9,642,953 B2
(45) Date of Patent: May 9, 2017

(54) DRESSINGS, SYSTEMS, AND METHODS FOR TREATING A TISSUE SITE

(71) Applicant: KCI Licensing, Inc., San Antonio, TX (US)

(72) Inventors: Tyler Simmons, San Antonio, TX (US); Alexander G. Sammons, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 370 days.

(21) Appl. No.: 14/230,487

(22) Filed: Mar. 31, 2014

(65) Prior Publication Data
US 2015/0025484 A1    Jan. 22, 2015

Related U.S. Application Data

(63) Continuation of application No. 13/043,315, filed on Mar. 8, 2011, now Pat. No. 8,721,606.
(Continued)

(51) Int. Cl.
*A61M 1/00* (2006.01)
*A61F 13/00* (2006.01)
(Continued)

(52) U.S. Cl.
CPC ..... *A61M 1/0088* (2013.01); *A61F 13/00021* (2013.01); *A61F 13/00068* (2013.01);
(Continued)

(58) Field of Classification Search
CPC ......... A61M 1/00; A61M 27/00; A61L 15/16; A61F 13/02
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
(Continued)

*Primary Examiner* — Michele Kidwell
*Assistant Examiner* — Ilya Treyger

(57) ABSTRACT

Dressings, systems, and methods are disclosed for treating tissue with reduced pressure. A dressing for distributing reduced pressure to a tissue site includes a plurality of liquid-impermeable layers that are stacked and a plurality of spacers disposed at least partially between adjacent liquid-impermeable layers. The plurality of liquid-impermeable layers are fenestrated at least in part. The plurality of spacers and plurality of liquid-impermeable layers form a plurality of flow paths for allowing fluid flow under reduced pressure. Adjacent layers of the plurality of liquid-impermeable layers are stacked without foam between at least a majority of coextensive surfaces. Other dressings, systems, and methods are disclosed.

31 Claims, 12 Drawing Sheets

Related U.S. Application Data

(60) Provisional application No. 61/312,968, filed on Mar. 11, 2010.

(51) Int. Cl.
    *A61M 27/00*     (2006.01)
    *A61L 15/16*     (2006.01)
    *A61F 13/02*     (2006.01)

(52) U.S. Cl.
    CPC   *A61F 13/00995* (2013.01); *A61F 2013/0054* (2013.01); *A61F 2013/00174* (2013.01); *A61F 2013/00327* (2013.01); *A61F 2013/00412* (2013.01); *A61F 2013/00536* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,951,553 B2 * | 10/2005 | Bubb .............. A61M 1/0088 601/6 |
| 8,398,614 B2 | 3/2013 | Blott et al. |
| 8,449,509 B2 | 5/2013 | Weston |
| 8,853,486 B2 | 10/2014 | Wild et al. |
| 8,926,592 B2 | 1/2015 | Blott et al. |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2006/0155260 A1 | 7/2006 | Blott et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |

(56) References Cited

FOREIGN PATENT DOCUMENTS

| WO | 94/20041 | 9/1994 |
|---|---|---|
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukia, Ž. Maksimovio, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

2

DRESSINGS, SYSTEMS, AND METHODS FOR TREATING A TISSUE SITE

RELATED APPLICATION

This is a continuation application of U.S. patent application Ser. No. 13/043,315 entitled "Dressings, Systems, and Methods for Treating a Tissue Site," filed Mar. 8, 2011, which claims the benefit, under 35 USC §119(e), of the filing of U.S. Provisional Patent Application Ser. No. 61/312,968, entitled "Dressings, Systems, and Methods for Treating a Tissue Site," filed Mar. 11, 2010, which is incorporated herein by reference for all purposes.

BACKGROUND

The present disclosure relates generally to medical treatment systems, and more particularly, to apparatuses, systems, and methods for treating tissue sites using reduced pressure.

Depending on the medical circumstances, reduced pressure may be used for, among other things, reduced-pressure therapy to encourage granulation at a tissue site or for draining fluids at a tissue site. As used herein, unless otherwise indicated, "or" does not require mutual exclusivity. Both reduced-pressure therapy and drainage with reduced pressure often involve manifolding, or distributing, reduced pressure to the tissue site.

SUMMARY

According to a non-limiting, illustrative embodiment, a dressing for distributing reduced pressure to a tissue site includes a plurality of liquid-impermeable layers that are stacked and a plurality of spacers disposed at least partially between adjacent liquid-impermeable layers. The plurality of liquid-impermeable layers are fenestrated. The plurality of spacers and plurality of liquid-impermeable layers form a plurality of flow paths for allowing fluid flow under reduced pressure. Adjacent layers of the plurality of liquid-impermeable layers may be stacked without foam between at least a majority of coextensive surfaces.

According to another non-limiting, illustrative embodiment, a system for distributing reduced pressure to a tissue site includes a reduced-pressure source, a reduced-pressure delivery conduit, and a reduced-pressure dressing. The reduced-pressure delivery conduit fluidly couples the reduced-pressure source and the reduced-pressure dressing. The reduced-pressure dressing includes a plurality of liquid-impermeable layers that are stacked and a plurality of spacers disposed at least partially between liquid-impermeable layers. The plurality of liquid-impermeable layers are fenestrated. The plurality of spacers and plurality of liquid-impermeable layers form a plurality of flow paths for allowing fluid flow under reduced pressure. Adjacent layers of the plurality of liquid-impermeable layers may be stacked without foam between at least a majority of coextensive surfaces.

According to another non-limiting, illustrative embodiment, a method of manufacturing a dressing for distributing reduced pressure to a tissue site includes the steps of: providing a plurality of liquid-impermeable layers, stacking the plurality of liquid-impermeable layers, and forming a plurality of spacers disposed at least partially between adjacent liquid-impermeable layers. The plurality of liquid-impermeable layers are fenestrated. The plurality of spacers and plurality of liquid-impermeable layers form a plurality of flow paths for allowing fluid flow under reduced pressure. Adjacent layers of the plurality of liquid-impermeable layers are stacked without foam between at least a majority of coextensive surfaces.

According to another non-limiting, illustrative embodiment, a method for delivering reduced pressure to a tissue site includes the steps of: providing a reduced-pressure dressing, deploying the reduced-pressure dressing adjacent to the tissue site, fluidly coupling a reduced-pressure source to the reduced-pressure dressing, and activating the reduced-pressure source. The reduced-pressure dressing includes a plurality of liquid-impermeable layers that are stacked and a plurality of spacers disposed at least partially between adjacent liquid-impermeable layers. The plurality of liquid-impermeable layers are fenestrated. The plurality of spacers and plurality of liquid-impermeable layers form a plurality of flow paths for allowing fluid flow under reduced pressure. Adjacent layers of the plurality of liquid-impermeable layers may be stacked without foam between at least a majority of coextensive surfaces.

Other features and advantages of the illustrative embodiments will become apparent with reference to the drawings and detailed description that follow.

DETAILED DESCRIPTION

In the following detailed description of the non-limiting, illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
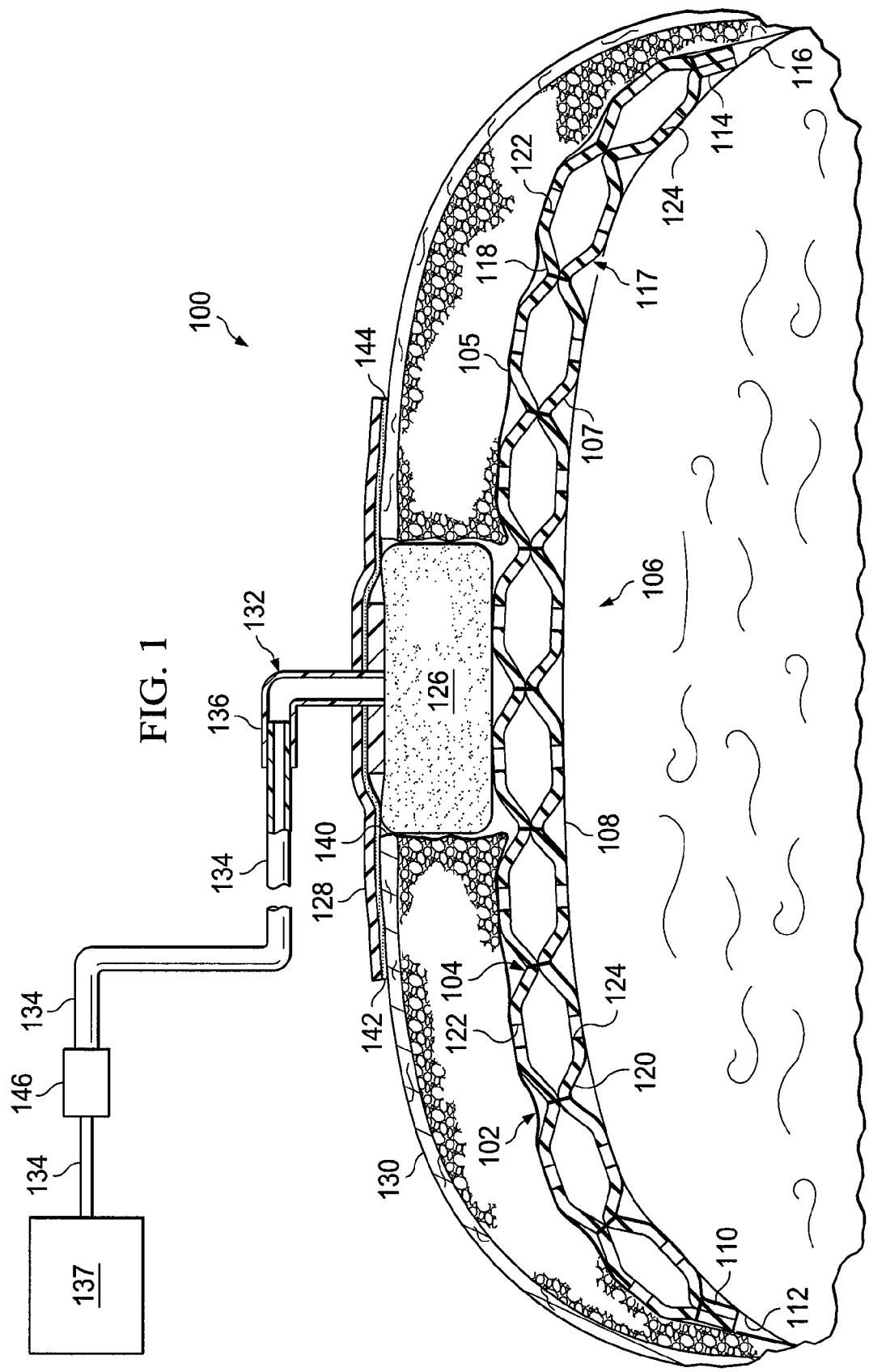
FIG. 1 is a schematic diagram with a portion shown in cross section of an illustrative embodiment of a reduced-pressure treatment system for treating an abdominal cavity.
Figure 2:
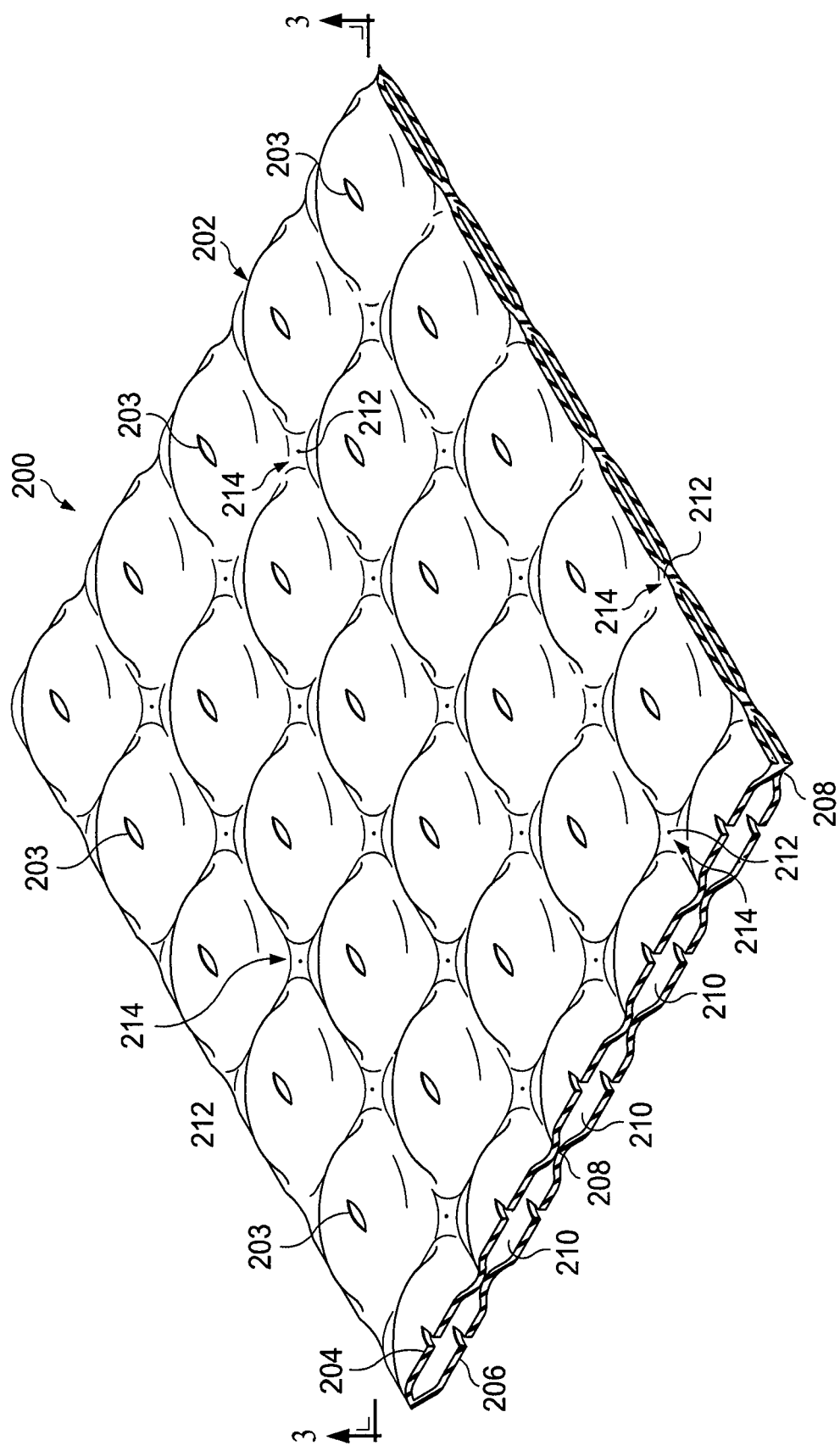
FIG. 2 is a schematic, perspective view of an illustrative dressing for use with reduced pressure.

Referring now to FIG. 1, an illustrative embodiment of a system 100 for treating an abdominal cavity 102 that includes an abdominal treatment device 104 is presented. The abdominal treatment device 104 may be, for example, an illustrative dressing 200 for use with reduced pressure as shown in FIG. 2. The system 100 and the abdominal treatment device 104 are for treating a tissue site 106 of a patient. The tissue site 106 may be the bodily tissue of any human, animal, or other organism, including bone tissue, adipose tissue, muscle tissue, dermal tissue, connective tissue, cartilage, tendons, ligaments, or any other tissue. In this illustrative embodiment, the tissue site 106 includes tissue in a body cavity, and in particular the abdominal cavity 102, and includes abdominal contents 108 or tissue that is proximate the abdominal cavity 102. Treatment of the tissue site 106 may include removal of fluids, e.g., ascites, protection of the abdominal cavity 102, or reduced-pressure therapy.

As shown, the abdominal treatment device 104 is disposed within the abdominal cavity 102 of the patient to treat the tissue site 106. The abdominal treatment device 104 is supported by the abdominal contents 108. The abdominal contents 108 make up a surface on which the abdominal treatment device 104 is placed. A portion 110 of the abdominal treatment device 104 may be placed in or proximate to a first paracolic gutter 112, and another portion 114 may be placed in or proximate to a second paracolic gutter 116. FIG. 1 is a schematic drawing and is not to scale and the density of flow paths would typically be higher.

The abdominal treatment device 104 is formed with a plurality of liquid-impermeable layers 117, e.g., a first liquid-impermeable layer 118 and a second liquid-impermeable layer 120. The plurality of liquid-impermeable layers 117, e.g., layers 118, 120, are formed with fenestrations 122, 124, respectively. "Liquid impermeable" with respect to "liquid-impermeable layers" means that the layers are formed with a liquid-impermeable material. Thus, although formed with a liquid-impermeable material, the layer may be liquid permeable when fenestrated, but nonetheless is referred to as a liquid-impermeable layer. The fenestrations 122, 124 may take any shape, e.g., circular apertures, rectangular openings, or polygons. The fenestrations 122, 124 are presented in this illustrative embodiment as slits, or linear cuts. Not every layer need be fenestrated. The abdominal treatment device 104 has a first side 105 and a second, tissue-facing side 107. The abdominal treatment device 104 is typically symmetrical such that the sides 105, 107 are same. Reference to different sides, however, is made for explanation purposes.

A manifold 126, or manifold pad, distributes reduced pressure to the abdominal treatment device 104. A sealing member 128 provides a fluid seal over the abdominal cavity 102. One or more skin closure devices may be placed on a patient's epidermis 130.

A reduced-pressure connector subsystem 132 may be used to fluidly couple the abdominal treatment device 104 to a reduced-pressure delivery conduit 134. The reduced-pressure connector subsystem 132 may include a reduced-pressure connector 136, or interface, and the manifold 126. Alternatively, the reduced-pressure connector subsystem 132 may be an in situ connector (not shown) on the abdominal treatment device 104 or any other device for supplying reduced pressure to the abdominal treatment device 104. The reduced-pressure delivery conduit 134 is fluidly coupled to a reduced-pressure source 137. In one illustrative embodiment, reduced pressure is delivered to the abdominal treatment device 104 through the manifold 126 which receives reduced pressure through the reduced-pressure connector 136, which is coupled to the reduced-pressure delivery conduit 134. The reduced-pressure source 137 delivers reduced pressure to the reduced-pressure delivery conduit 134.

The reduced pressure may be applied to the tissue site 106 to help promote removal of ascites, exudates, or other fluids from the tissue site 106. In some instances, reduced pressure may be applied to stimulate the growth of additional tissue. In some instances, only fluid removal may be desired. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site.

The manifold 126 is shown adjacent to the abdominal treatment device 104. The manifold 126 may take many forms. The term "manifold" as used herein generally refers to a substance or structure that is provided to assist in applying reduced pressure to, delivering fluids to, or removing fluids from the tissue site 106 directly or via the abdominal treatment device 104. The manifold 126 typically includes a plurality of flow channels or pathways that distribute the fluids provided to and removed from the tissue site 106 around the manifold 126 and through the abdominal treatment device 104. In one illustrative embodiment, the flow channels or pathways are interconnected to improve distribution of fluids provided or removed. The manifold 126 may be a biocompatible material that is capable of being placed in contact with the tissue site 106 and distributing reduced pressure to the tissue site 106 or abdominal treatment device 104. Examples of manifold 126 may include, without limitation, devices that have structural elements arranged to form flow channels, cellular foam, such as open-cell foam, porous tissue collections, liquids, gels and foams that include or cure to include flow channels. The manifold 126 may be porous and may be made from foam, gauze, felted mat, or any other material suited to a particular biological application. In one embodiment, the manifold 126 is a porous foam and includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. Other embodiments may include "closed cells." In some situations, the manifold 126 may also be used to distribute fluids, such as medications, antibacterials, growth factors, and various solutions. Other layers may be included in or on the manifold 126, such as absorptive materials, wicking materials, hydrophobic materials, and hydrophilic materials.

The sealing member 128 is placed over the abdominal cavity 102 and provides a fluid seal. As used herein, "fluid seal," or "seal," means a seal adequate to maintain reduced pressure at a desired site given the particular reduced-pressure source or subsystem involved. The sealing member 128 may be a cover, or drape, that is used to secure the manifold 126 on a portion of the abdominal treatment device 104. The sealing member 128 may be impermeable or semi-permeable. The sealing member 128 is capable of maintaining reduced pressure at the tissue site 106 or other desired location after installation of the sealing member 128 over the abdominal cavity 102 and particularly an abdominal cavity opening 140. The sealing member 128 may be a flexible over-drape or film formed from a silicone-based compound, acrylic, hydrogel or hydrogel-forming material, polyurethane, polymer film, or any other biocompatible material that includes the impermeability or permeability characteristics as desired for applying reduced pressure to the tissue site 106.

The sealing member 128 may further include an attachment device 142 to couple the sealing member 128 to the patient's epidermis 130. The attachment device 142 may take many forms. For example, the attachment device 142 may be an adhesive layer 144 that may be positioned along a perimeter of the sealing member 128 or any portion of the sealing member 128 to provide, directly or indirectly, a fluid seal with the patient's epidermis 130. The adhesive layer 144 may also be pre-applied to the sealing member 128 and covered with a releasable backing, or member (not shown), that is removed at the time of application.

The reduced-pressure connector 136 may be, as one example, a port or connector, which permits the passage of fluid from the manifold 126 to the reduced-pressure delivery conduit 134 and vice versa. For example, fluid collected from the tissue site 106 using the manifold 126 and the abdominal treatment device 104 may enter the reduced-pressure delivery conduit 134 via the reduced-pressure connector 136. In another embodiment, the system 100 may omit the reduced-pressure connector 136 and the reduced-pressure delivery conduit 134 may be inserted directly into the sealing member 128 and into the manifold 126. The reduced-pressure delivery conduit 134 may be a medical conduit or tubing or any other means for transportating a reduced pressure and fluid. The reduced-pressure delivery conduit 134 may be a multi-lumen member for readily delivering reduced pressure and removing fluids. In one embodiment, the reduced-pressure delivery conduit 134 is a two-lumen conduit with one lumen for reduced pressure and liquid transport and one lumen for communicating pressure to a pressure sensor.

Reduced pressure is generated and supplied to the reduced-pressure delivery conduit 134 by the reduced-pressure source 137. A wide range of reduced pressures may be generated or supplied by the reduced-pressure source 137. In one illustrative embodiment, the reduced pressure is in the range of −50 to −300 mm Hg and in another illustrative embodiment, the range may include −100 mm Hg to −200 mm Hg. The pressure may be, for example, −100, −110, −120, −125, −130, −140, −150, −160, −170, −180, −190, or −200 mm Hg. In one illustrative embodiment, the reduced-pressure source 137 includes preset selectors for −100 mm Hg, −125 mm Hg, and −150 mm Hg. The reduced-pressure source 137 may also include a number of alarms, such as a blockage alarm, a leakage alarm, canister full alarm, or a battery-low alarm. The reduced-pressure source 137 may be a portable source, wall source, or other unit for abdominal cavities or other tissue sites. The reduced-pressure source 137 may selectively deliver a constant pressure, varied pressure, intermittent pressure, or continuous pressure. The fluid removed from the abdominal cavity 102 through the reduced-pressure delivery conduit 134 could be as much as 5L or more per day depending on the circumstances. A fluid reservoir is typically associated with the reduced-pressure source 137 for receiving fluids.

A number of different devices, e.g., device 146, may be added to a portion of the reduced-pressure delivery conduit 134. For example, the device 146 may be a fluid reservoir, or canister collection member, a pressure-feedback device, a volume detection system, a blood detection system, an infection detection system, a filter, a port with a filter, a flow monitoring system, a temperature monitoring system, etc. Multiple devices 146 may be included. Some of these devices, e.g., the fluid collection member, may be formed integrally to the reduced-pressure source 137.

Referring now primarily to FIG. 2, an illustrative, non-limiting embodiment of a dressing 200 that may be used in many situations to distribute reduced pressure and remove fluids is presented. The dressing 200 may be a modular component used in systems or devices. For example, the dressing 200 may be used as the abdominal treatment device 104 of FIG. 1 or as the manifold member 302 in FIG. 7. The dressing 200 includes a plurality of liquid-impermeable layers 202, such as a first liquid-impermeable layer 204 and a second liquid-impermeable layer 206, and a plurality of spacers 208.

The plurality of liquid-impermeable layers 202 may include fenestrations 203, which may be formed with any shape and size. The fenestrations 203 allow the egress of reduced pressure and the ingress of fluids. The plurality of liquid-impermeable layers 202 may be formed from numerous materials including the materials used for the sealing member 128 of FIG. 1.

The plurality of spacers 208 may be disposed (including formed or positioned) at least partially between adjacent members of the plurality of liquid-impermeable layers 202. "Partially" means to some extent or degree. The plurality of spacers 208 may be formed by portions of the impermeable layers themselves bonded to hold portions of adjacent layers with a relative displacement or may be formed by the layers being folded or in other ways as shown and described herein. Reference to spacers "between" layers means the portions displacing the layers or portions of the layers are at least partially located between the exterior of adjacent layers. For example, a fold has a curved portions between the exteriors of two layers that may be formed from a single layer of material. Thus, the spacer may be said to be between layers even when formed by portions of the layers. The plurality of spacers 208 provide areas of separation between adjacent members of the plurality of liquid-impermeable layers 202 and thereby help create a plurality of flow paths 210. The figures are not to scale, and it should be understood that the flow paths 210 may be much more dense than shown. For example, the flow paths 210 may be only one millimeter apart, two millimeters apart, three millimeters apart, four millimeters a part, or another dimension.

The plurality of spacers 208 and plurality of liquid-impermeable layers 202 form the plurality of flow paths 210 for allowing fluid flow under reduced pressure or positive pressure. Adjacent layers of the plurality of liquid-impermeable layers 202 are typically stacked. "Stacked" generally means disposing or forming layers to be adjacent. In some embodiments, foam or other material with flow paths may be included between the liquid-impermeable layers 202. For example, the first liquid-impermeable layer 204 and the second liquid-impermeable layer 206 may share an area $A_1$ and the foam may have an area $A_2$ that is in the range of 0% to 50% of $A_1$ and often includes no foam (i.e., 0% $A_1$).

The plurality of spacers 208 may be formed in numerous ways including by forming a plurality of bonds 212 at a plurality of bond sites 214. The plurality of bonds 212 may be formed using any known technique, including without limitation welding (e.g., ultrasonic or RF welding), chemical bonding, adhesives, or cements. The plurality of bond sites 214 may be random or may have a spaced pattern. The plurality of bonds 212 may have a longitudinal dimension, a lateral dimension, and a vertical dimension (for the orientation shown). The plurality of bonds 212 may have an aspect ratio (longitudinal dimension/lateral dimension) greater than 3, or greater than 6, or greater still. The plurality of bonds 212 may also be circular in nature or any other shape.

Figure 3:
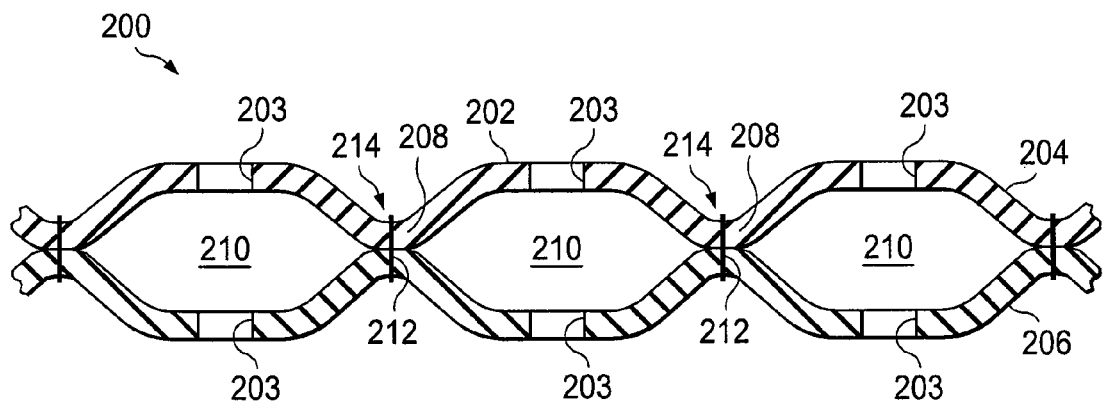
FIG. 3 is a schematic cross section of a portion of the illustrative dressing of FIG. 2 shown without reduced pressure applied.
Figure 4:
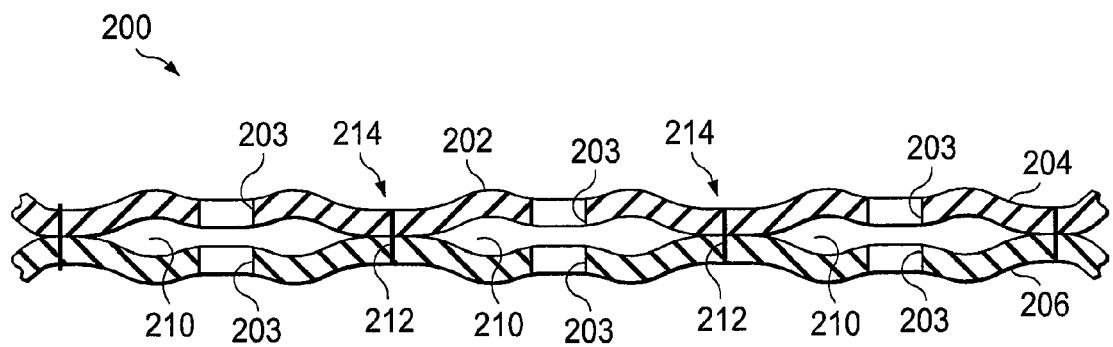
FIG. 4 is a schematic cross section of the portion of the illustrative dressing of FIG. 3 shown with reduced pressure applied.

Referring now primarily to FIG. 3, a detail of a portion of the dressing 200 of FIG. 2 is presented. The dressing 200 is shown without reduced pressure applied. FIG. 4 shows the same detail as FIG. 3, but with reduced pressure applied. The reduced pressure may draw portions of the adjacent members of the plurality of liquid-impermeable layers 202 closer together, but at least a portion of the plurality of flow paths 210 continue to provide a flow path that may transport reduced pressure and fluids.

Figure 5:
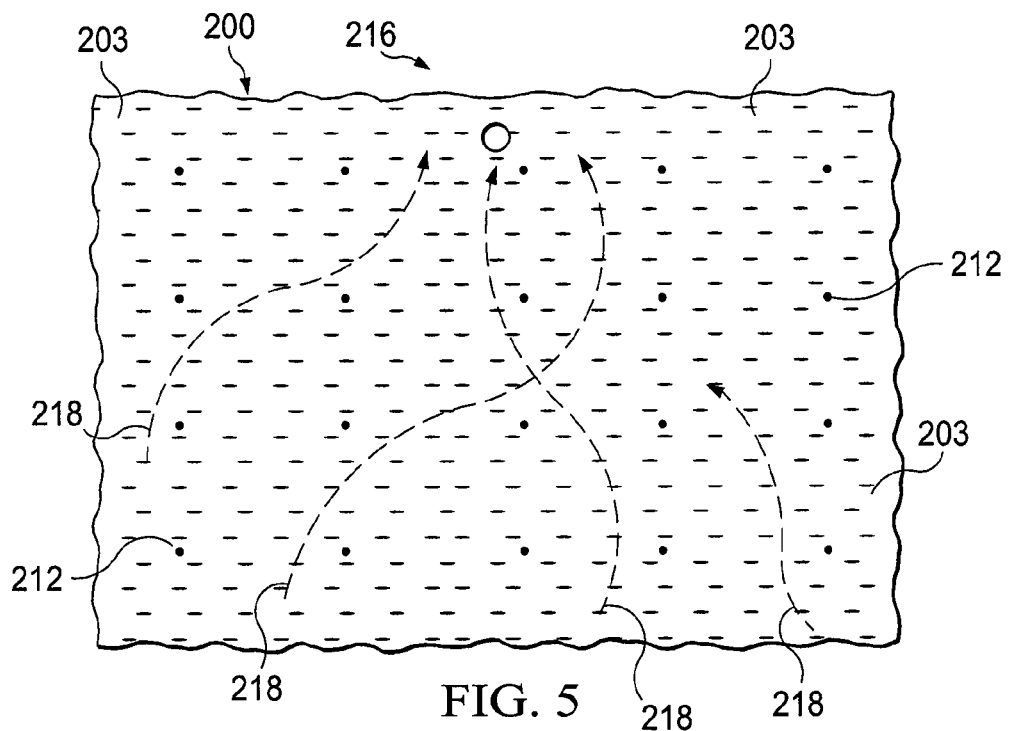
FIG. 5 is a schematic diagram showing various flow paths in an illustrative embodiment of a dressing for use with reduced pressure.

Referring now primarily to FIG. 5, a schematic plan view showing one possible flow pattern for a portion of the dressing 200 is presented. A reduced-pressure aperture 216 delivers reduced pressure between adjacent layers of the plurality of liquid-impermeable layers 202 and pulls or urges liquid through fenestrations 203 from a tissue site or cavity and then along the plurality of flow paths 210 (FIG. 3) to allow flows streams 218 to reach the reduced-pressure aperture 216.

Figure 6:
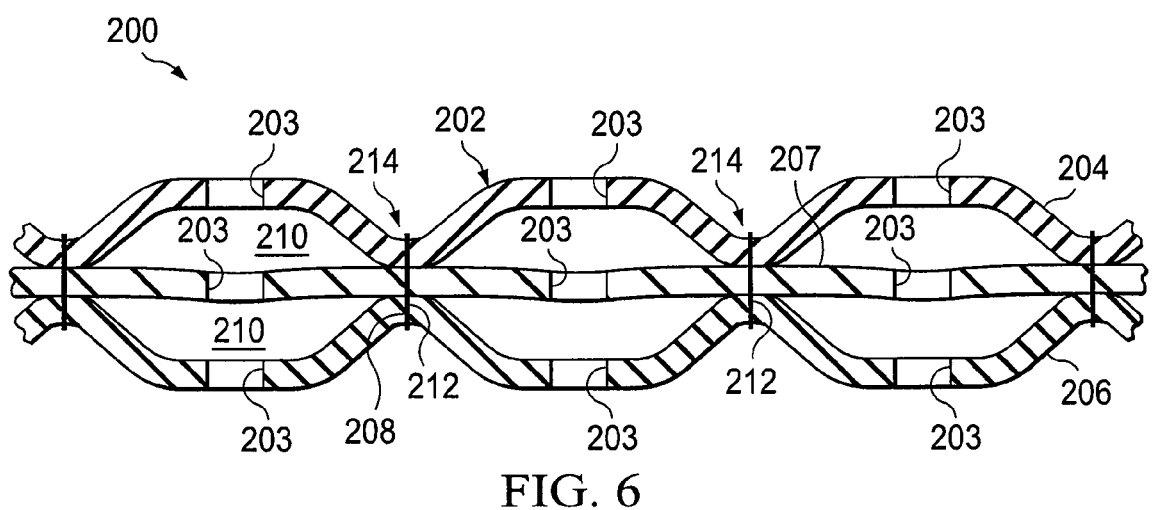
FIG. 6 is a schematic cross section of a portion of an illustrative dressing for use with reduced pressure.

Referring now primarily to FIG. 6, the dressing 200 is shown with the plurality of liquid-impermeable layers 202 including the first liquid-impermeable layer 204, a second liquid-impermeable layer 206, and a third liquid-impermeable layer 207. The fenestrations 203 may or may not be through the third liquid-impermeable layer 207. In other words, some layers, e.g., third liquid-impermeable layer 207 may not be fenestrated. Additional layers may be added to the plurality of liquid-impermeable layers 202. The spacers 208 provide at least some separation between adjacent layers of the plurality of liquid-impermeable layers 202 to define flow paths 210.

Figure 7:
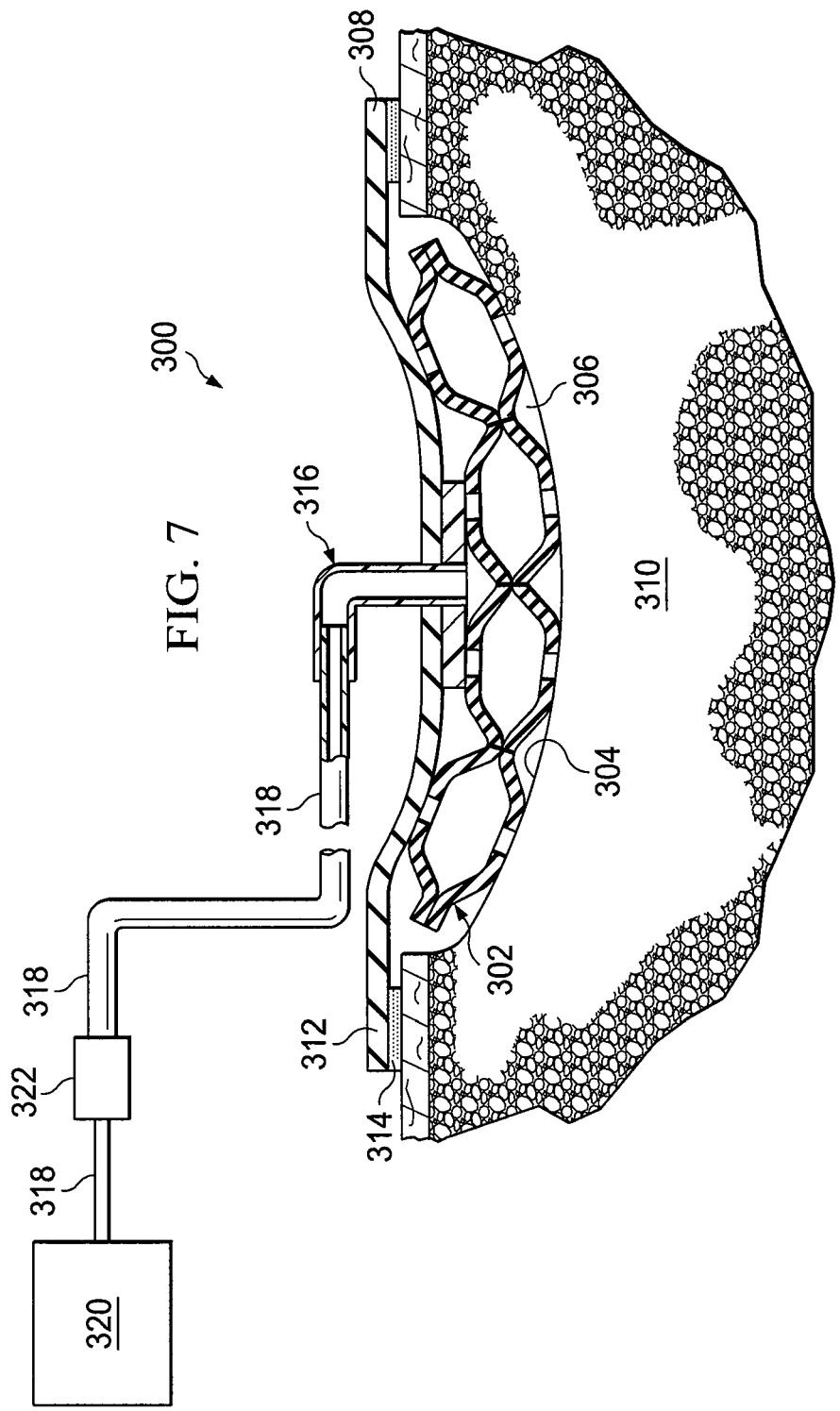
FIG. 7 is a schematic diagram with a portion shown in cross section of an illustrative embodiment of a reduced-pressure treatment system for treating a wound.

Referring now primarily to FIG. 7, an illustrative, non-limiting example of a reduced-pressure treatment system 300 is presented that includes a manifold member 302. The manifold member 302 may be the dressing 200 of FIG. 2. The reduced-pressure treatment system 300 provides reduced pressure to a tissue site 304, such as an open wound 306. The wound 306 may extend through epidermis 308 and into subcutaneous tissue 310.

The manifold member 302 is placed adjacent to the tissue site 304 and then is covered with a sealing member 312. An attachment device 314 may be used to help provide a fluid seal over the tissue site 304. A connector subsystem 316 may fluidly couple a reduced-pressure delivery conduit 318 and the manifold member 302. The reduced-pressure delivery conduit 318 is also fluidly coupled to a reduced-pressure source 320. A device 322 may be fluidly coupled or otherwise associated with the reduced-pressure delivery conduit 318.

The device 322 is the same or analogous to the device 146 of FIG. 1. Moreover, many of the components of the system 300 of FIG. 3 are identical or analogous to components of the system 100 of FIG. 1. As another example, the sealing member 312 is analogous to the sealing member 128. The attachment device 314 is analogous to the attachment device 142 of FIG. 1.

In operation, the manifold member 302 is placed adjacent to the tissue site 304. The sealing member 312 is applied over the tissue site 304 and a fluid seal is thereby formed. If not already applied, the reduced-pressure connector subsystem 316 is applied to the sealing member 312. If not already installed, the reduced-pressure delivery conduit 318 is fluidly coupled to the reduced-pressure connector subsystem 316 and to the reduced-pressure source 320. The reduced-pressure source 320 is activated. The reduced pressure is communicated to the manifold member 302 and causes reduced pressure to be delivered to the tissue site 304 through a plurality of flow paths (see flow paths 210 in FIG. 2) and fenestrations (see fenestrations 203 in FIG. 2). Fluids collected thereby are removed through reduced-pressure delivery conduit 318. Various micro-stress-inducing elements may be added to the tissue-facing side of the manifold member 302 to promote granulation. The micro-stress-inducing elements may include small buttons, projecting columns, or other devices.

Figure 8:
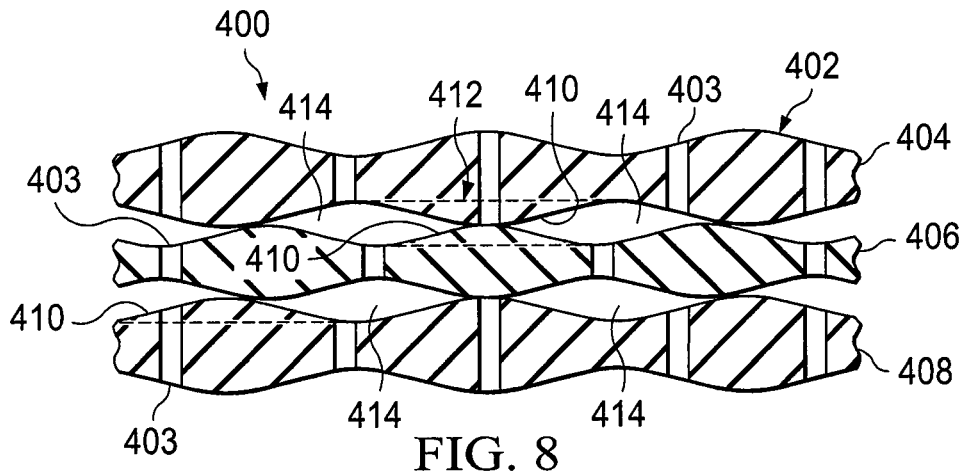
FIG. 8 is a schematic cross section of a portion of an illustrative dressing for use with reduced pressure.

Referring now primarily to FIG. 8, a portion of another illustrative, non-limiting embodiment of a dressing 400 is presented. The dressing 400 includes a plurality of liquid-impermeable layers 402, e.g., a first liquid-impermeable layer 404, a second liquid-impermeable layer 406, and a third liquid-impermeable layer 408. The plurality of liquid-impermeable layers 402 is fenestrated with fenestrations 403. The plurality of liquid-impermeable layers 402 are formed with thickness variations or enlarged portions 410 that form spacers 412. Under reduced pressure, the spacers 412 continue to provide a plurality of flow paths 414. The plurality of flow paths 414 function analogously to flow paths 210 of FIG. 2.

Figure 9:
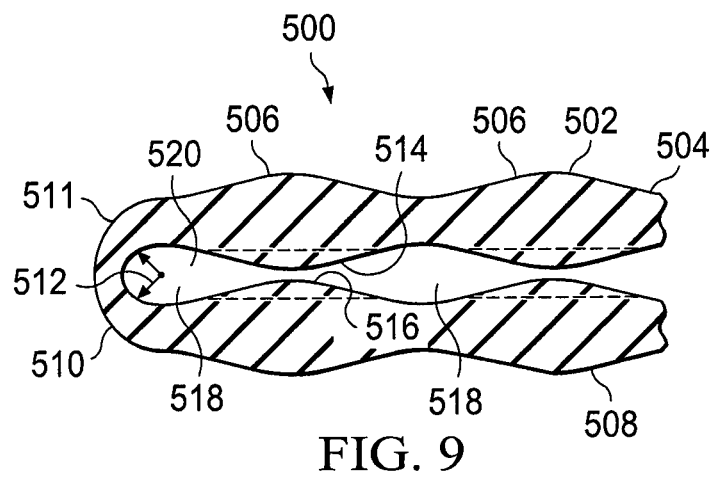
FIG. 9 is a schematic cross section of a portion of an illustrative dressing for use with reduced pressure showing a fold.

Referring now primarily to FIG. 9, another portion of an illustrative, non-limiting embodiment of a dressing 500 is presented. The dressing 500 is formed with a plurality of liquid-impermeable layers 502. In this illustrative embodiment, the plurality of liquid-impermeable layers 502 are formed by doubling, or folding, a first liquid-impermeable layer 504 over on itself to form a first portion 506 and a second portion 508. The plurality of liquid-impermeable layers 502 is fenestrated (not explicitly shown but analogous to fenestrations 403 in FIG. 8).

A fold 510 has a curved portion 511 with a radius 512. The dressing 500 may have a plurality of folds, such as fold 510. The folds, e.g., 510, serve as spacers. The radius 512 is relatively larger when thicker materials or more rigid materials are used for the plurality of liquid-impermeable layers 502. The radius 512 forms a micro-channel 520, which may be one of a plurality of flow paths 518. The first liquid-impermeable layer 504 may be formed with enlarged portions, e.g., enlarged portions 514 and 516 that help define the plurality of flow paths 518. The radius 512 may also form or help form one of the flow paths 518. The flow paths 518 may be formed by a plurality of enlarged portions, e.g., enlarged portions 514, 516, or a plurality of folds, e.g., the fold 510 or both.

Figure 10:
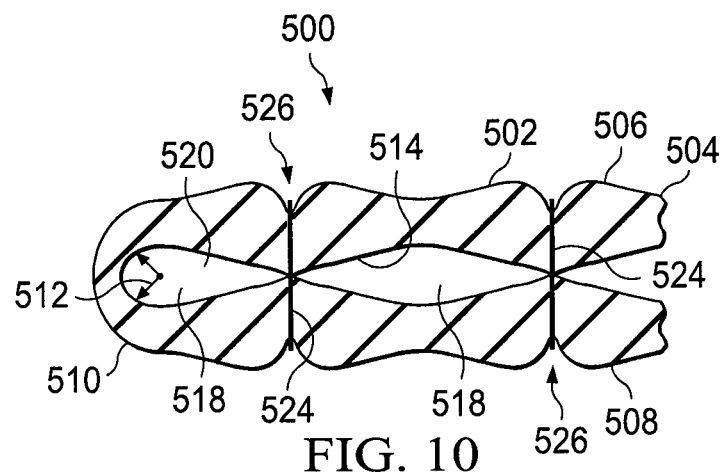
FIG. 10 is a schematic cross section of a portion of an illustrative dressing for use with reduced pressure.
Figure 11:
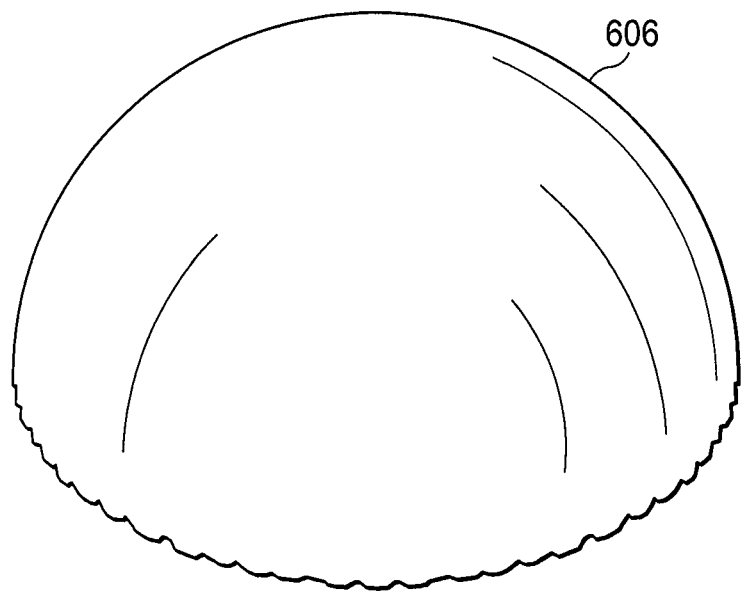
FIG. 11 is a schematic, perspective view of a generic curved body part or a portion of a curved body part.
Figure 13:
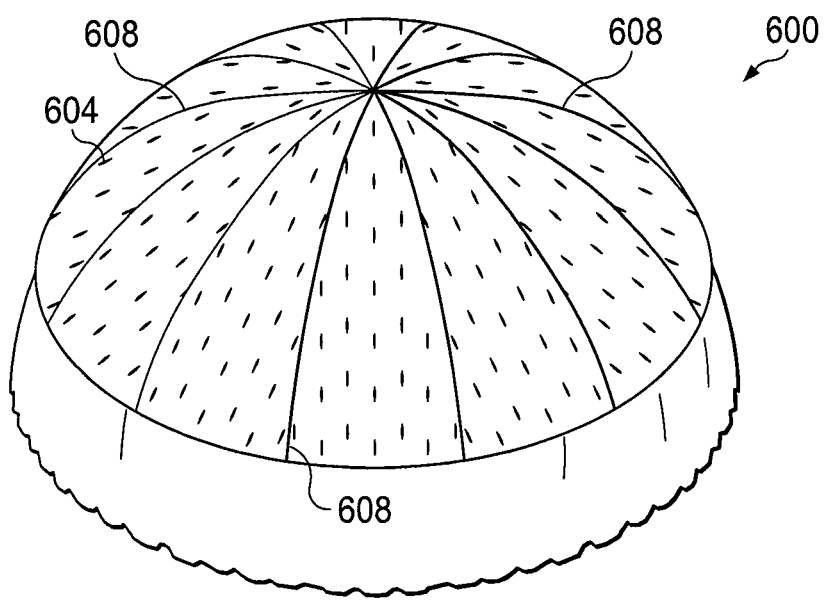
FIG. 13 is a schematic, perspective view of the illustrative dressing of FIG. 12 shown applied to the curved body part of FIG. 11.

FIG. 10 shows the dressing 500 of FIG. 9, but a plurality of bonds 524 has been added at a plurality of bond sites 526. As an alternative or addition, the flow paths 518 may be formed in dressing 500 by folding the first liquid-impermeable layer 504 on itself, stretching either the first portion 506 relative to the second portion 508 (or vice versa) and then adding the plurality of bonds 524. Once bonded, the portion of the first liquid-impermeable layer 504 in tension may be released. This release will then form a plurality of flow paths 518 between the plurality of bonds 524.

Referring now primarily to FIGS. 11-15, another illustrative, non-limiting embodiment of a dressing 600 is presented. The dressing 600 may be used with numerous reduced-pressure systems, such as in the system 100 of FIG. 1 as the abdominal treatment device 104, or in the system 300 of FIG. 3 as the manifold member 302. Generally, the dressing 600 creates folds 608 by requiring a two-dimensional flat layer 602 to form to a three-dimensional body part, or curved body part 606. The folds 608 comprise channels, or flow paths 612. The folds 608 of the dressing 600 facilitate fluid movement.

Figure 12:
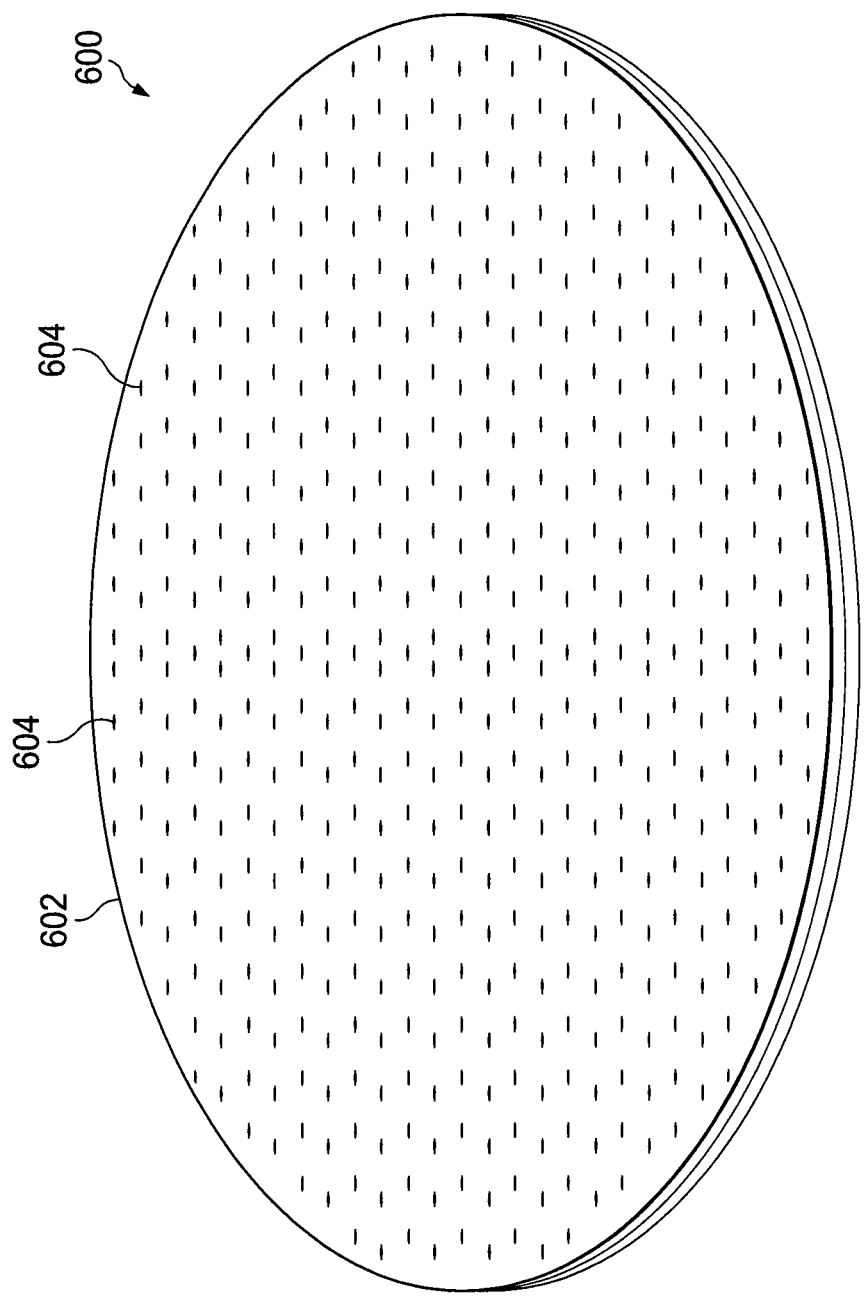
FIG. 12 is a schematic, perspective view of an illustrative dressing for use with reduced pressure shown in a flat arrangement.

The dressing 600 is formed with the two-dimensional flat layer 602, or liquid-impermeable layer 602. The liquid-impermeable layer 602 has fenestrations 604. The fenestrations 604 allow the egress of reduced pressure and the ingress of fluids. The liquid-impermeable layer 602 may be formed from any suitable material, such as those mentioned in connection with the liquid-impermeable layers 118, 120, 204, and 206 of FIGS. 1 and 2. The liquid-impermeable layer 602 may be single ply, double ply, or multi-ply. As shown in FIG. 12, the dressing 600 may be formed as a flat oval, but other shapes, e.g., a circle, square, or irregular shape, may be used. While referenced as a two-dimensional flat layer 602, the two-dimensional flat layer 602 will have some thickness but will rest flat on a flat surface.

The dressing 600 is for use with the curved body part 606. The curved body 606 may be any part of a patient that is not flat and that typically has a substantial curvature. Referring now primarily to FIG. 12, as the liquid-impermeable layer 602 is deployed flush against the curved body part 606, the folds 608, or plurality of folds, are created. As shown clearly in FIGS. 14 and 15, the plurality of folds 608 that develop in order for the dressing 600 to rest flush against the curved body part 606, create the channels or flow paths 612. The folds 608 comprise a plurality of spacers 610 that provide areas of separation between portions of the liquid-impermeable layer 602 to define the plurality of flow paths 612. The flow paths 612 may function as micro-channels that facilitate fluid movement.

Figure 14:
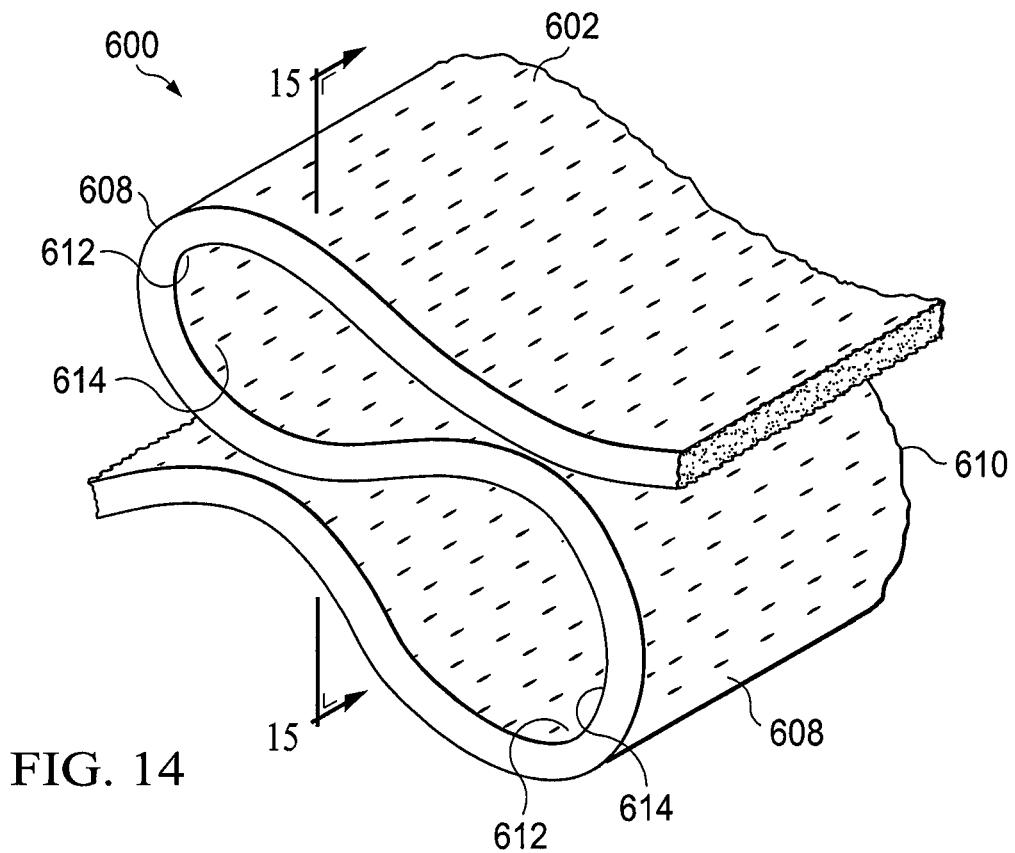
FIG. 14 is a schematic, perspective view with a portion shown in cross section of a fold in the illustrative dressing of FIG. 13.
Figure 15:
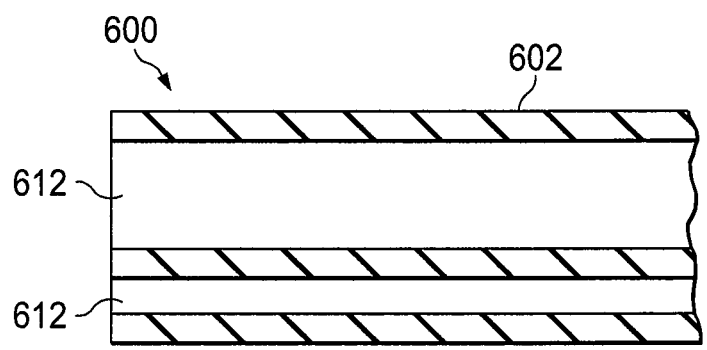
FIG. 15 is a schematic, cross section of a fold in the illustrative dressing of FIG. 14 taken along line 15-15.

Referring now primarily to FIG. 14, a perspective view of one of the plurality of folds 608 of the dressing 600 is shown. In this illustrative embodiment, the liquid-impermeable layer 602 is a single-ply layer and two folds 608 are shown. Again, the liquid-impermeable layer 602 may be a multi-layer member. The folds 608 comprise spacers 610 and the resultant openings of the folds serve as the micro-channels. FIG. 15 presents a cross section of the portion of the dressing 600 shown in FIG. 14.

Figure 16:
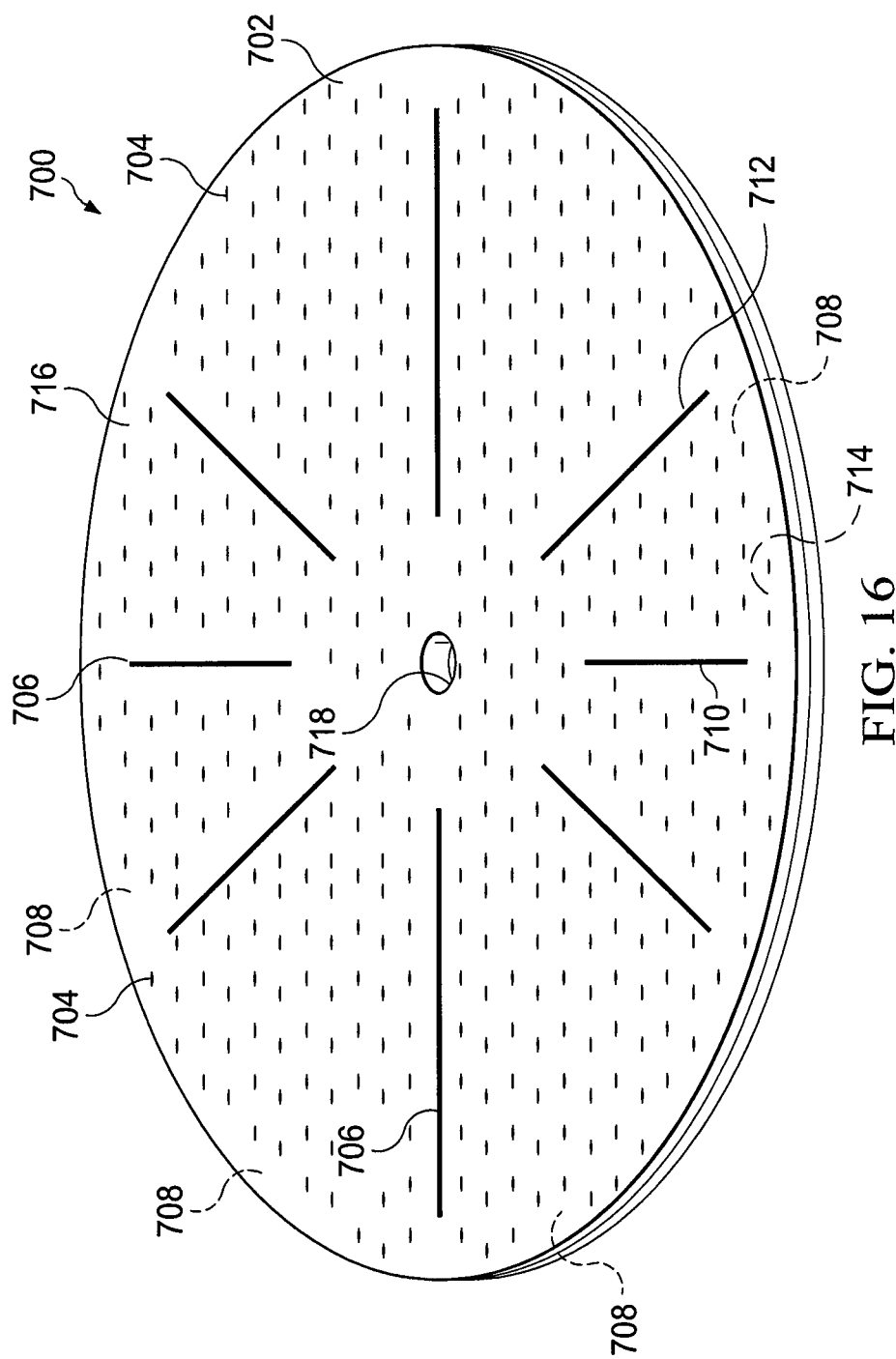
FIG. 16 is a schematic, perspective view of an illustrative dressing for use with reduced pressure showing illustrative flow channels.

Referring primarily now to FIG. 16, another illustrative embodiment of a dressing 700 is presented that may be used with numerous reduced-pressure systems, such as systems 100 and 300 of FIGS. 1 and 3. The dressing 700 may be formed with a plurality of liquid-impermeable layers 702 that have fenestrations 704. A plurality of spacers, e.g., spacers 208 of FIG. 2, may be formed between adjacent layers of the plurality of liquid-impermeable layers 702 to form a plurality of flow paths (not shown but analogous to the flow paths 210 of FIG. 2). A plurality of longitudinal members or bonds 706 may be formed on the plurality of liquid-impermeable layers 702 to form a plurality of flow channels 708. For example, a first longitudinal bond 710 and a second longitudinal bond 712, which is spaced from the first longitudinal bond 710, form a flow channel 714. A first side 716 may be formed with a reduced-pressure aperture 718 to facilitate fluidly coupling a reduced-pressure source (not shown). The flow channels 708 direct fluid flowing in flow paths along directed areas of the dressing 700.

Figure 17:
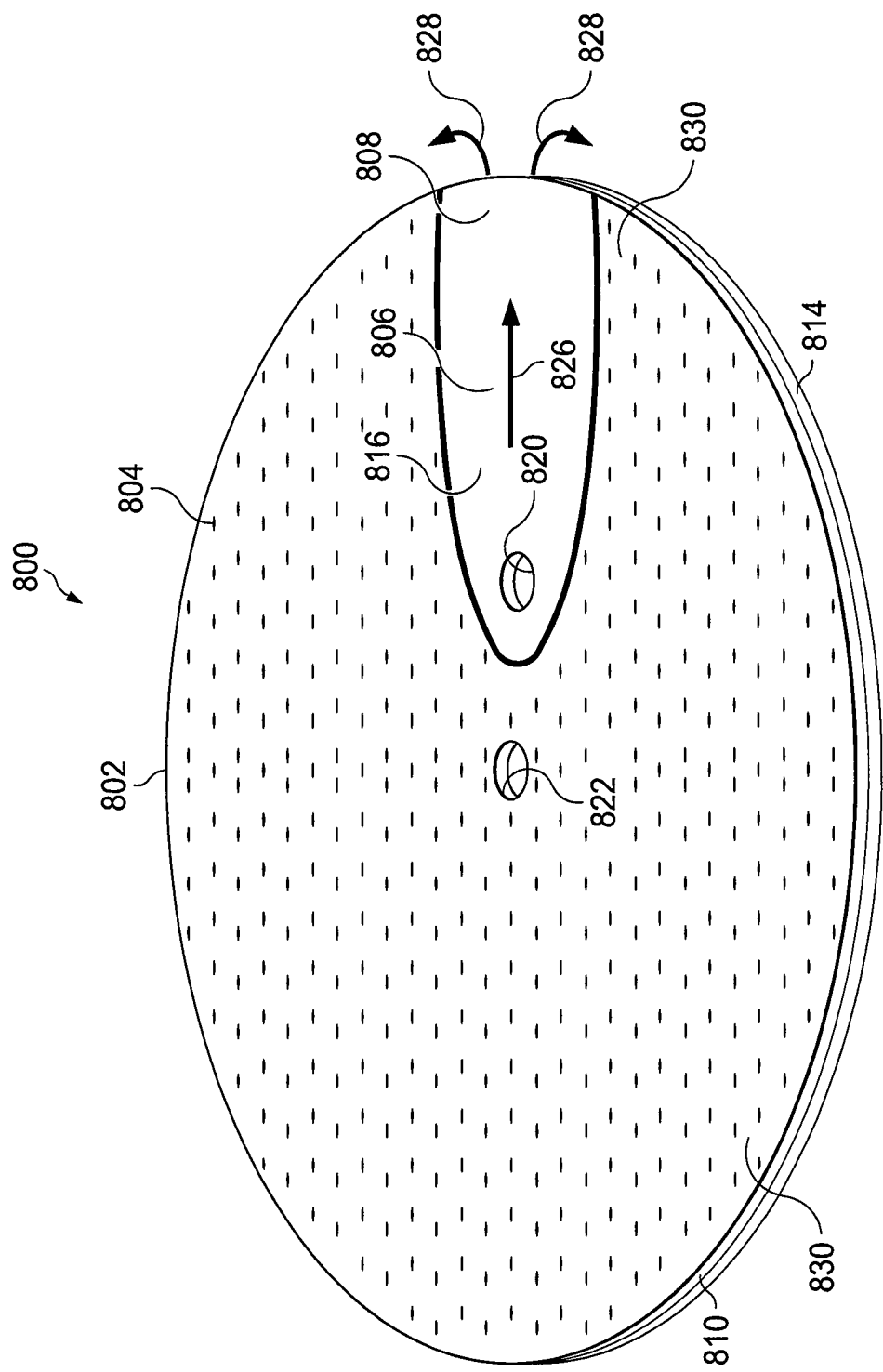
FIG. 17 is a schematic, perspective view of an illustrative dressing for use with reduced pressure showing an illustrative liquid-delivery channel.
Figure 18:
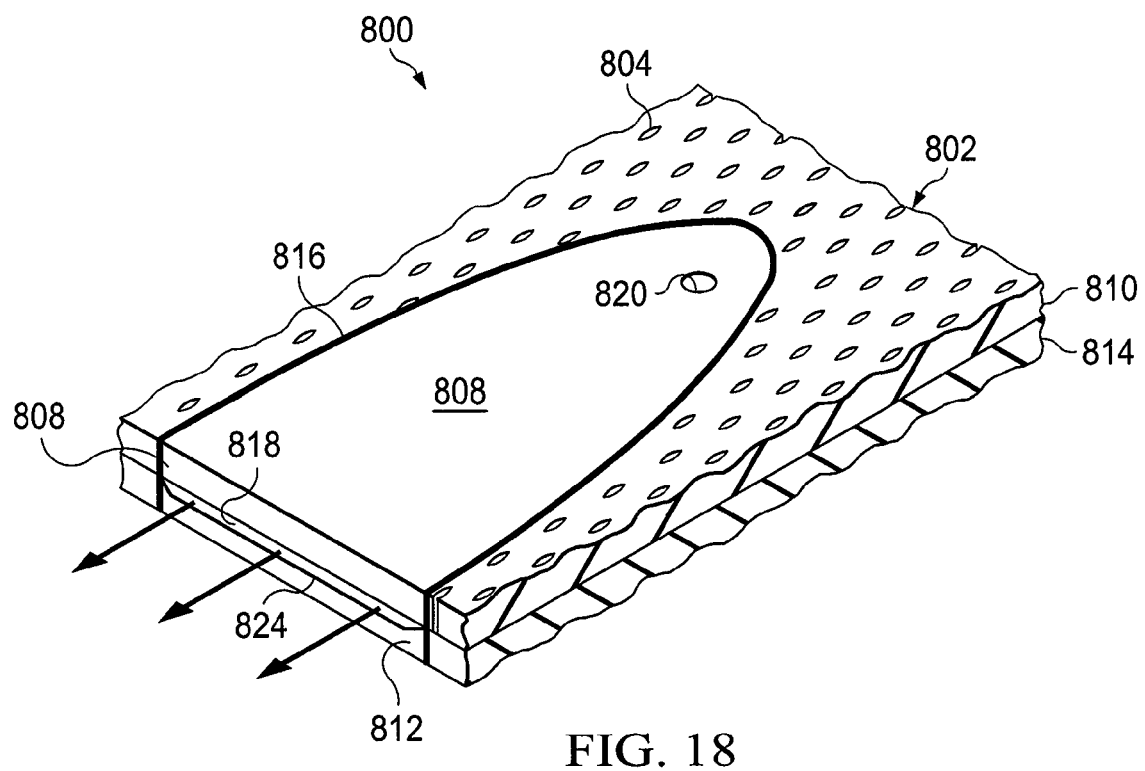
FIG. 18 is schematic, perspective view of a portion of the illustrative dressing of FIG. 17 showing the peripheral edge of the illustrative liquid-delivery channel.

Referring now primarily to FIGS. 17 and 18, another illustrative, non-limiting embodiment of a dressing 800 is presented. The dressing 800 may be formed with a plurality of liquid-impermeable layers 802. The plurality of liquid-impermeable layers 802 may have fenestrations 804 and may be bonded at bonded sites analogous to bonds 212 at bond sites 214 in FIG. 2. The dressing 800 may include a liquid-delivery channel 806.

The liquid-delivery channel 806 may include a first portion 808. The first portion 808 is part of a first liquid-impermeable layer 810 of the plurality of liquid-impermeable layers 802, but without fenestrations 804. The liquid-delivery channel 806 also includes a second portion 812. The second portion 812 is part of a second liquid-impermeable layer 814 of the plurality of liquid-impermeable layers 802, and again the second liquid-impermeable layer 814 has no fenestrations 804. A channel-forming bond 816 is formed that couples the first portion 808 and the second portion 812 to form a liquid delivery path 818. A liquid aperture 820 may be formed on the first liquid-impermeable layer 810 to facilitate fluidly coupling of a liquid-supply source (not shown) to the liquid-delivery channel 806.

In operation, according to one illustrative embodiment, the dressing 800 is deployed as part of a reduced-pressure treatment system proximate the tissue site to be treated. A reduced-pressure source (not shown) is fluidly coupled to a reduced-pressure aperture 822 to provide reduced pressure to the dressing 800. The reduced pressure pulls fluids into the dressing 800 except for the liquid-delivery channel 806. A fluid-supply source (not shown) is fluidly coupled to the liquid aperture 820. Liquid, e.g., a saline irrigation fluid or medicine, is delivered to the liquid aperture 820. Under the influence of reduced pressure experienced at a peripheral edge 824, liquid delivered to the liquid aperture 820 is urged through the liquid delivery path 818 toward the peripheral edge 824 and exits the liquid delivery channel 806 as suggested by arrows 826 and 828 in FIG. 17. The fluid exiting 828 is pulled through a second portion 830 of the dressing 800 through the fenestrations 804 and toward the reduced-pressure aperture 822. The liquid-delivery channel 806 may be used to irrigate, supply medicines, or other purposes.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claimed:

1. A dressing for distributing reduced pressure to a tissue site, the dressing comprising:
    at least two layers that are liquid impermeable and positioned in a stacked relationship, each layer having one or more fenestrations through the layer; and
    a plurality of bonds coupling the at least two layers, the bonds spacing portions of adjacent layers with a relative displacement to form a plurality of flow pathways, each bond having a longitudinal dimension, a lateral dimension, and a vertical dimension, the longitudinal dimension and the lateral dimension having an aspect ratio greater than about three.

2. The dressing of claim 1, wherein the aspect ratio is greater than about six.

3. The dressing of claim 1, further comprising a third layer disposed between the at least two layers and coupled to the at least two layers by the plurality of bonds.

4. The dressing of claim 3, wherein the third layer further comprises one or more fenestrations through the third layer.

5. The dressing of claim 1, wherein at least one of the at least two layers further comprises one or more micro-stress inducing elements formed on a surface of the layer opposite the other of the at least two layers.

6. The dressing of claim 5, wherein the micro-stress inducing elements comprise at least one of buttons and projecting columns.

7. The dressing of claim 1, wherein a thickness of each layer is variable.

8. The dressing of claim 1, wherein the at least two layers comprise a single layer folded with a curved portion having a radius.

9. The dressing of claim 8, wherein the radius forms a micro-channel extending along at least one edge of the dressing.

10. A system for distributing reduced pressure to a tissue site, the system comprising:
    a reduced-pressure source;
    a conduit configured to be fluidly coupled to the reduced-pressure source;
    a dressing configured to be fluidly coupled to the reduced-pressure source by the conduit, the dressing comprising:
        at least two layers that are liquid impermeable and positioned in a stacked relationship, each layer having one or more fenestrations through the layer; and
        a plurality of bonds coupling the at least two layers, the bonds spacing portions of adjacent layers with a relative displacement to form a plurality of flow pathways, each bond having a longitudinal dimension, a lateral dimension, and a vertical dimension, the longitudinal dimension and the lateral dimension having an aspect ratio greater than about three.

11. The system of claim 10, wherein the aspect ratio is greater than about six.

12. The system of claim 10, further comprising a third layer disposed between the at least two layers and coupled to the at least two layers by the plurality of bonds.

13. The system of claim 12, wherein the third layer further comprises one or more fenestrations through the third layer.

14. The system of claim 10, wherein at least one of the at least two layers further comprises one or more micro-stress inducing elements formed on a surface of the layer opposite the other of the at least two layers.

15. The system of claim 14, wherein the micro-stress inducing elements comprises at least one of buttons and projecting columns.

16. The system of claim 10, wherein a thickness of each layer is variable.

17. The system of claim 10, wherein the at least two layers comprise a single layer folded with a curved portion having a radius.

18. The system of claim 17, wherein the radius forms a micro-channel extending along at least one edge of the dressing.

19. A dressing for distributing reduced pressure to a tissue site, the dressing comprising:
    a first layer and a second layer that are liquid impermeable and having one or more fenestrations through the first layer and the second layer;
    a plurality of bonds coupling the first layer to the second layer, each bond spaced from adjacent bonds and being longitudinal, wherein pairs of bonds that are adjacent form at least one flow channel; and
    wherein the first layer and the second layer are configured to conform to a surface having a substantial curve by forming one or more folds, the one or more folds forming one or more micro-channels configured to facilitate fluid movement.

20. The dressing of claim 19, wherein the at least one layer is circular.

21. The dressing of claim 19, wherein the first layer and the second layer have a circular shape and are coextensive.

22. The dressing of claim 19, wherein:
    the first layer and the second layer each include a portion without fenestrations;
    the portions without fenestrations are coextensive; and
    the dressing further comprises:
        a channel-forming bond coupling the first layer and the second layer, the channel-forming bond disposed between the portions without fenestrations and a portion with fenestrations to form a liquid delivery path, and
        a liquid aperture formed in the first layer and in fluid communication with the liquid delivery path.

23. The dressing of claim 22, wherein the liquid aperture is configured to be fluidly coupled to a fluid source.

24. A system for distributing reduced pressure to a tissue site, the system comprising:
    a reduced-pressure source;

a conduit configured to be fluidly coupled to the reduced-pressure source;

a dressing configured to be fluidly coupled to the reduced-pressure source by the conduit, the dressing comprising:

a first layer and a second layer that are liquid impermeable and having one or more fenestrations through the first layer and the second layer;

a plurality of bonds coupling the first layer to the second layer, each bond spaced from adjacent bonds and being longitudinal, wherein pairs of bonds that are adjacent form at least one flow channel; and wherein the first layer and the second layer are configured to conform to a surface having a substantial curve by forming one or more folds, the one or more folds forming one or more micro-channels configured to facilitate fluid movement.

25. The system of claim 24, wherein the at least one layer is circular.

26. The system of claim 24, wherein the first layer and the second layer have a circular shape and are coextensive.

27. The system of claim 24, wherein:

the first layer and the second layer each include a portion without fenestrations;

the portions without fenestrations are coextensive; and the dressing further comprises:

a channel-forming bond coupling the first layer and the second layer, the channel-forming bond disposed between the portions without fenestrations and a portion with fenestrations to form a liquid delivery path, and a liquid aperture formed in the first layer and in fluid communication with the liquid delivery path.

28. The system of claim 27, further comprising a fluid source configured to be fluidly coupled to the liquid aperture.

29. A dressing for distributing reduced pressure to a tissue site, the dressing comprising:

a first liquid-impermeable layer having first fenestrations;

a second liquid-impermeable layer having second fenestrations; and a plurality of spacers disposed between the first liquid-impermeable layer and the second liquid-impermeable layer, the plurality of spacers providing separation between the first liquid-impermeable layer and the second liquid-impermeable layer and defining flow paths between the first fenestrations and the second fenestrations.

30. The dressing of claim 29, wherein the plurality of spacers comprise bonds between the first liquid-impermeable layer and the second liquid-impermeable layer.

31. The dressing of claim 29, wherein at least one of the first liquid-impermeable layer and the second liquid impermeable layer comprise a polymer film.

* * * * *